US 8,041,426 B2

(12) United States Patent
Fogoros et al.

(10) Patent No.: US 8,041,426 B2
(45) Date of Patent: Oct. 18, 2011

(54) SELECTIVE RESYNCHRONIZATION THERAPY OPTIMIZATION BASED ON USER PREFERENCE

(75) Inventors: Richard Fogoros, Pittsburg, PA (US); Jiang Ding, Shoreview, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 127 days.

(21) Appl. No.: 12/565,344

(22) Filed: Sep. 23, 2009

(65) Prior Publication Data

US 2010/0010557 A1 Jan. 14, 2010

Related U.S. Application Data

(62) Division of application No. 11/109,603, filed on Apr. 19, 2005, now Pat. No. 7,613,514.

(51) Int. Cl.
*A61N 1/365* (2006.01)

(52) U.S. Cl. ............................................. 607/24; 607/18

(58) Field of Classification Search ................. 607/9, 18, 607/23, 24, 25
See application file for complete search history.

(56) References Cited

U.S. PATENT DOCUMENTS

| 5,174,289 | A | 12/1992 | Cohen |
| 5,282,838 | A | 2/1994 | Hauser et al. |
| 5,330,511 | A | 7/1994 | Boute |
| 5,334,222 | A | 8/1994 | Salo et al. |
| 5,466,245 | A | 11/1995 | Spinelli et al. |
| 5,507,782 | A | 4/1996 | Kieval et al. |
| 5,507,784 | A | 4/1996 | Hill et al. |
| 5,514,163 | A | 5/1996 | Markowitz et al. |
| 5,527,347 | A | 6/1996 | Shelton et al. |
| 5,540,727 | A | 7/1996 | Tockman et al. |
| 5,626,620 | A | 5/1997 | Kieval et al. |
| 5,626,623 | A | 5/1997 | Kieval et al. |
| 5,643,327 | A | 7/1997 | Dawson et al. |
| 5,690,689 | A | 11/1997 | Sholder |
| 5,716,383 | A | 2/1998 | Kieval et al. |
| 5,749,906 | A | 5/1998 | Kieval et al. |
| 5,800,471 | A | 9/1998 | Baumann |
| 5,861,007 | A | 1/1999 | Hess et al. |
| 5,873,895 | A | 2/1999 | Sholder et al. |
| 5,902,324 | A | 5/1999 | Thompson et al. |
| 6,081,747 | A | 6/2000 | Levine et al. |

(Continued)

FOREIGN PATENT DOCUMENTS

WO     WO-99/58191 A1    11/1999

(Continued)

OTHER PUBLICATIONS

"U.S. Appl. No. 11/109,603, Advisory Action mailed Nov. 26, 2008", 3 pgs.

(Continued)

*Primary Examiner* — Scott Getzow
*Assistant Examiner* — Joseph Dietrich
(74) *Attorney, Agent, or Firm* — Schwegman, Lundberg & Woessner, P.A.

(57) ABSTRACT

A method and system for calculating an atrio-ventricular delay interval based upon an inter-atrial delay exhibited by a patient's heart. The aforementioned atrio-ventricular delay interval may optimize the stroke volume exhibited by a patient's heart. The aforementioned atrio-ventricular delay interval may be blended with another atrio-ventricular delay interval that may optimize another performance characteristic, such as left ventricular contractility. Such blending may include finding an arithmetic mean, geometric mean, or weighted mean of two or more proposed atrio-ventricular delay intervals.

20 Claims, 6 Drawing Sheets

U.S. PATENT DOCUMENTS

| | | | |
|---|---|---|---|
| 6,144,880 | A | 11/2000 | Ding et al. |
| 6,167,307 | A | 12/2000 | Hess |
| 6,311,088 | B1 | 10/2001 | Betzold et al. |
| 6,351,673 | B1 | 2/2002 | Ding et al. |
| 6,360,127 | B1 | 3/2002 | Ding et al. |
| 6,449,510 | B1 | 9/2002 | Albers et al. |
| 6,498,949 | B2 | 12/2002 | Levine et al. |
| 6,507,756 | B1 | 1/2003 | Heynen et al. |
| 6,542,775 | B2 | 4/2003 | Ding et al. |
| 6,567,700 | B1 | 5/2003 | Turcott et al. |
| 6,574,506 | B2 | 6/2003 | Kramer et al. |
| 6,597,951 | B2 | 7/2003 | Kramer et al. |
| 6,604,000 | B2 | 8/2003 | Lu |
| 6,654,637 | B2 | 11/2003 | Rouw et al. |
| 6,684,103 | B2 | 1/2004 | Ding et al. |
| 6,751,504 | B2 | 6/2004 | Fishler |
| 6,792,307 | B1 | 9/2004 | Levine et al. |
| 6,792,308 | B2 | 9/2004 | Corbucci |
| 6,804,555 | B2 | 10/2004 | Warkentin |
| 6,856,836 | B2 | 2/2005 | Ding et al. |
| 6,859,665 | B2 | 2/2005 | Ding et al. |
| 6,871,088 | B2 | 3/2005 | Chinchoy |
| 6,871,096 | B2 | 3/2005 | Hill |
| 6,882,882 | B2 | 4/2005 | Struble et al. |
| 6,937,895 | B1 | 8/2005 | Lu |
| 6,947,794 | B1 | 9/2005 | Levine |
| 7,013,176 | B2 | 3/2006 | Ding et al. |
| 7,020,522 | B1 | 3/2006 | Hoijer et al. |
| 7,020,524 | B1 | 3/2006 | Bradley |
| 7,047,073 | B2 | 5/2006 | Hoijer et al. |
| 7,065,406 | B1 | 6/2006 | Gustavsson |
| 7,069,079 | B2 | 6/2006 | Struble et al. |
| 7,079,895 | B2 | 7/2006 | Verbeek et al. |
| 7,079,896 | B1 | 7/2006 | Park et al. |
| 7,110,817 | B2 | 9/2006 | Yu et al. |
| 7,123,960 | B2 | 10/2006 | Ding et al. |
| 7,142,922 | B2 | 11/2006 | Spinelli et al. |
| 7,158,830 | B2 | 1/2007 | Yu et al. |
| 7,177,687 | B2 | 2/2007 | Schuller |
| 7,184,835 | B2 | 2/2007 | Kramer et al. |
| 7,203,540 | B2 | 4/2007 | Ding et al. |
| 7,215,998 | B2 | 5/2007 | Wesselink et al. |
| 7,228,174 | B2 | 6/2007 | Burnes et al. |
| 7,236,824 | B2 | 6/2007 | Rouw et al. |
| 7,239,915 | B2 | 7/2007 | Cohen |
| 7,245,969 | B2 | 7/2007 | Lincoln et al. |
| 7,248,925 | B2 | 7/2007 | Bruhns et al. |
| 7,613,514 | B2 | 11/2009 | Fogoros et al. |
| 7,869,873 | B2 | 1/2011 | Ding et al. |
| 2003/0078628 | A1 | 4/2003 | Holmstrom et al. |
| 2003/0144702 | A1 | 7/2003 | Yu et al. |
| 2003/0144703 | A1 | 7/2003 | Yu et al. |
| 2003/0204212 | A1 | 10/2003 | Burnes et al. |
| 2004/0019365 | A1 | 1/2004 | Ding et al. |
| 2004/0024423 | A1 | 2/2004 | Lincoln et al. |
| 2004/0030356 | A1 | 2/2004 | Osypka |
| 2004/0078059 | A1 | 4/2004 | Ding et al. |
| 2004/0078060 | A1 | 4/2004 | Ding et al. |
| 2004/0147966 | A1 | 7/2004 | Ding et al. |
| 2005/0131472 | A1 | 6/2005 | Ding et al. |
| 2005/0137632 | A1 | 6/2005 | Ding et al. |
| 2005/0137634 | A1 | 6/2005 | Hall et al. |
| 2005/0209648 | A1 | 9/2005 | Burnes et al. |
| 2006/0047320 | A1 | 3/2006 | Ding et al. |
| 2006/0235481 | A1 | 10/2006 | Fogoros et al. |
| 2006/0241706 | A1 | 10/2006 | Yonce et al. |
| 2006/0259086 | A1 | 11/2006 | Yu et al. |
| 2006/0271119 | A1 | 11/2006 | Ni et al. |
| 2006/0271121 | A1 | 11/2006 | Ding et al. |
| 2006/0276847 | A1 | 12/2006 | Yu et al. |
| 2007/0088401 | A1 | 4/2007 | Spinelli et al. |
| 2007/0135854 | A1 | 6/2007 | Kramer et al. |
| 2007/0142869 | A1 | 6/2007 | Perschbacher et al. |
| 2007/0150013 | A1 | 6/2007 | Ding et al. |
| 2010/0069988 | A1 | 3/2010 | Ding et al. |
| 2011/0106202 | A1 | 5/2011 | Ding et al. |

FOREIGN PATENT DOCUMENTS

| | | |
|---|---|---|
| WO | WO-2004/011088 A1 | 2/2004 |
| WO | WO-2004/069333 A2 | 8/2004 |

OTHER PUBLICATIONS

"U.S. Appl. No. 11/109,603, Non-Final Office Action mailed Jan. 16, 2008", 9 pgs.

"U.S. Appl. No. 11/109,603, Non-Final Office Action mailed Feb. 11, 2009", 12 pgs.

"U.S. Appl. No. 11/109,603, Notice of Allowance mailed Jun. 29, 2009", 4 pgs.

"U.S. Appl. No. 11/109,603, Response filed Jan. 7, 2008 to Restriction Requirement mailed Dec. 6, 2007", 7 pgs.

"U.S. Appl. No. 11/109,603, Response filed Apr. 20, 2009 to Non-Final Office Action mailed Feb. 11, 2009", 10 pgs.

"U.S. Appl. No. 11/109,603, Response filed Jun. 16, 2008 to Non-Final Office Action mailed Jan. 16, 2008", 9 pgs.

"U.S. Appl. No. 11/109,603, Response filed Nov. 17, 2008 to Final Office Action mailed Sep. 17, 2008", 8 pgs.

"U.S. Appl. No. 11/109,603, Restriction Requirement mailed Dec. 6, 2007", 7 pgs.

"U.S. Appl. No. 11/109,603, Final Office Action mailed Sep. 17, 2008", 10 pgs.

Auricchio, A., "Effect of Pacing Chamber and Atrioventricular Delay on Acute Systolic Function of Paced Patients With Congestive Heart Failure", *Circulation*, 99(23), (Jun. 15, 1999), 2993-3001.

SELECTIVE RESYNCHRONIZATION THERAPY OPTIMIZATION BASED ON USER PREFERENCE

CROSS REFERENCE TO RELATED APPLICATION

This application is a divisional of U.S. application Ser. No. 11/109,603, now issued as U.S. Pat. No. 7,613,514, filed Apr. 19, 2005, which is hereby incorporated by reference in its entirety.

TECHNICAL FIELD

This present invention relates to cardiac rhythm management devices generally, and more particularly to cardiac pacing systems that employ an atrio-ventricular delay based in part upon a measured inter-atrial delay.

BACKGROUND

FIG. 1 depicts a human heart 100. As can be seen from FIG. 1, the heart 100 includes four chambers, the right and left atria 102 and 104, respectively, and the right and left ventricles 106 and 108, respectively. The heart 100 pumps so as to circulate blood through the human body in the following manner. Blood flows from the peripheral venous system to the right atrium 102. From the right atrium 102, blood passes through the tricuspid valve 110 to the right ventricle 106. Blood exits the right ventricle 106 through the pulmonary artery and is directed through the lungs, so that the blood may be reoxygenated. Oxygenated blood from the lungs is drawn from the pulmonary vein to the left atrium 104. From the left atrium, blood passes though the mitral valve 112 to the left ventricle 108. Finally, the blood flows from the left ventricle 108, through the aortic valve, to the peripheral arterial system in order to transfer oxygenated blood to the organs of the body.

To cause the blood to circulate in the above-described manner, electrical pulses propagate through the heart 100, causing the various cardiac muscle cells to contract when excited by the pulses. Usually, the cycle of electrical excitation of the heart 100 is initiated by the sinoatrial node 114. An electrical impulse is generated by the sinoatrial node 114. The impulse propagates from the sinoatrial node 114 to the right and left atria 102 and 104. As a consequence of normal propagation, the right and left atria 102 and 104 contract at substantially the same time. Contraction of the atria 102 and 104 force blood from the right and left atria 102 and 104 into the right and left ventricles 106 and 108, respectively. Eventually, the electrical impulse reaches the atrioventricular node 116. From the atrioventricular node 116, the electrical impulse is carried along right and left bundle branch fibers (not depicted) to a network of fast-conducting Purkinje fibers (not depicted) that extend throughout most of the endocardial surface of the ventricles 106 and 108. The ventricles 106 and 108, when excited by the electrical impulse, contract at substantially the same time, causing the blood therein to exit and travel to either the lungs or the peripheral arterial system, as mentioned above.

Efficiency of heart function may be influenced by several factors. Amongst those factors is synchrony between the chambers of the heart. Efficient heart function is encouraged by atrio-ventricular synchrony, meaning that the ventricles 106 and 108 should contract shortly after contraction of the atria 102 and 104. Premature ventricular contraction may lead to inefficiency because the ventricles 106 and 108 do not become fully filled with blood before contraction. On the other hand, retarded ventricular contraction may permit some of the blood contained in the ventricles 106 and 108 to flow back into the atria 102 and 104 prior to ventricular contraction—an effect that is also inimical to efficient heart function.

Efficient heart function is also encouraged by interventricular synchrony. The right and left ventricles 106 and 108 share a wall in common, the septum 118. Should the right ventricle 106 contract prior to contraction of the left ventricle 108, the septum 118 may initially contract with the right ventricle 106, shifting to the right. Then, upon contraction of the left ventricle 108, the septum 118 may contract with the left ventricle 108, and shift to the left. Thus, the septum 118 may exhibit a sort of "waffling" action, shifting first to the right and then to the left. Such waffling yields an inefficient cardiac stroke.

To encourage proper synchrony amongst the ventricles 106 and 108 or atria 102 and 104, cardiac resynchronization therapy may be employed by a cardiac rhythm management device, such as a pacemaker or defibrillator with pacing capabilities. Herein, the terms pacemaker, pulse generator device, and cardioverter/defibrillator (with pacing functionality) are used interchangeably and refer to a cardiac rhythm management device. Cardiac resynchronization therapy involves pacing one or both ventricles 106 and 108 in order to synchronize their contraction with one another or with one or both of the atria 102 and 104.

One important variable governing cardiac resynchronization therapy is an atrio-ventricular pacing delay interval that is employed by the device applying the resynchronization therapy. As explained in more detail, below, the atrio-ventricular pacing delay interval is responsible for determining the timing of pacing of one or both of the ventricles relative to a paced or sensed event occurring in the right atrium 102.

In atrial tracking and AV sequential pacing modes, a ventricular escape interval is defined between atrial and ventricular events. This escape interval is the aforementioned atrio-ventricular pacing delay interval or AVD interval, where a ventricular pacing pulse is delivered upon expiration of the atrio-ventricular pacing delay interval if no ventricular sense occurs before such expiration. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that the AVD interval starts with either an atrial pace or sense.

SUMMARY OF THE INVENTION

Against this backdrop, the present invention was developed. A method of arriving at a blended atrio-ventricular delay value may include the following acts. A first atrio-ventricular delay value selected to approximately maximize contractility of a ventricle may be determined. Next, a second atrio-ventricular delay value selected to approximately maximize stroke volume of the ventricle may be determined. Finally, the first and second atrio-ventricular delay values may be combined.

According to another embodiment, a system may include a cardiac rhythm management device. The system may also include a first lead having an electrode configured to make electrical contact with a region in the right atrium of a heart. The first lead may be configured to be coupled to the cardiac rhythm management device. The system may also include a second lead having an electrode configured to pass through and electrically contact the mid-coronary sinus of the heart before electrically contacting a left ventricle of the heart. The second lead may be configured to be coupled to the cardiac rhythm management device. Finally, the system may include a programmer configured to communicated data with the cardiac rhythm management device. The programmer includes instructions that perform a mode of operation, during which, signals from the second lead are interpreted as indicating left atrial activity, and upon termination of the mode of operation, signals from the second lead are interpreted as indicating left ventricular activity. The inter-atrial delay is determined by finding a span of time separating a paced or sensed event in the right atrium and a signal from the second lead indicating left atrial activity.

According to another embodiment a method of implanting a cardiac rhythm management device may include implanting a first lead so that an electrode therein makes electrical contact with a region within a right atrium of a heart. Next, a second lead is implanted so that a first electrode thereof makes electrical contact with the mid-coronary sinus of the heart and a second electrode thereof makes electrical contact with a first region of a left ventricle of the heart. Finally, the first and second leads are coupled to a cardiac rhythm management device.

DETAILED DESCRIPTION

Figure 1:
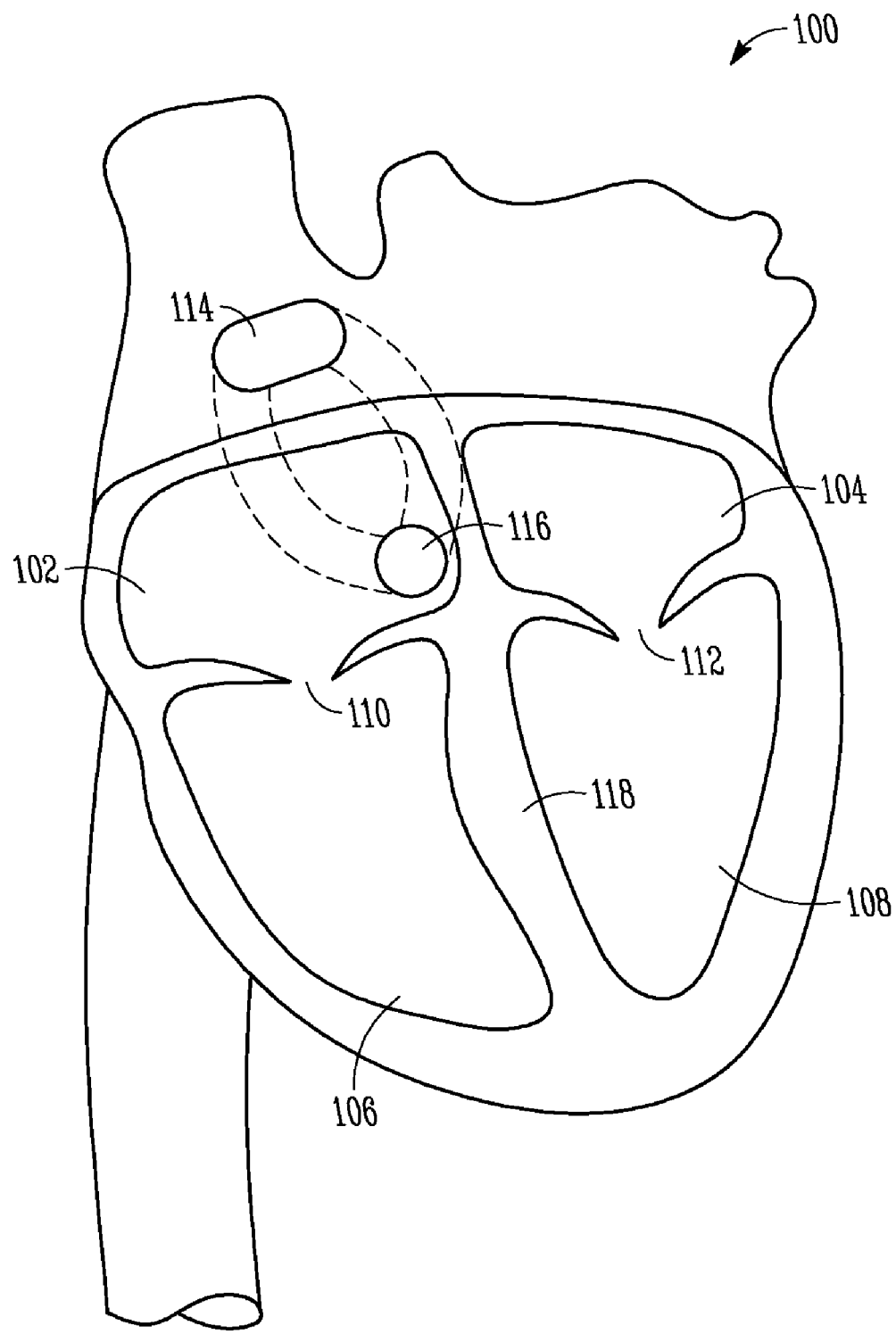
FIG. 1 depicts a human heart.

Heart function efficiency may be characterized in different ways, including characterization according to the left ventricular contractility or according to stroke volume. Briefly, left ventricular contractility indicates the capacity of the ventricular to contract (i.e., to squeeze, and therefore to force blood through the peripheral arterial system). Stroke volume, on the other hand, measures the volume of blood passing through the aorta (and to the peripheral arterial system), with each stroke of the heart.

In some instances, it is possible that one particular AVD interval optimizes a given patient's heart function, as understood by left ventricular contractility, while another AVD interval optimizes that patient's heart function, as understood by stroke volume. For instance, a patient may exhibit a cardiac condition wherein propagation of electrical impulses from the right atrium 102 to the left atrium 104 is dramatically slowed. For example, in an ordinary heart, such propagation may transpire over a time interval on the order of 30-50 milliseconds, while a defective heart may exhibit a propagation time on the order of 100-200 milliseconds. In a heart exhibiting such a condition, the right atrium 102 contracts prior to contraction of the left atrium 104. Consequently, blood exits the right atrium 102 and fills the right ventricle 106, prior to blood exiting the left atrium 104 and filling the left ventricle 108. In such a circumstance, it may be desirable to employ an AVD interval of sufficient length to ensure that the left ventricle 108 has an opportunity to fill with blood prior to contraction. By permitting the left ventricle 108 to fill with blood prior to contraction, it stands to reason that a relatively larger volume of blood should be forced from the left ventricle upon its contraction. Thus, it is possible that stroke volume is improved or maximized by employment of such an AVD interval. An AVD interval achieving the such a goal is a function of the inter-atrial propagation delay, or any signal or physiological event in predictable relation to the inter-atrial propagation delay. In other words, $$AVD_{stroke\ volume} = f(\text{inter-atrial delay}),$$

where $AVD_{stroke\ volume}$ represents an AVD interval maximizing stroke volume for a given patient and lead configuration or pacing chamber.

On the other hand, a heart may exhibit a condition known as left bundle branch block. In such a heart, the right ventricle 106 contracts prior to contraction of the left ventricle 108. As described above, this may result in a waffling action of the septum 118. To alleviate this condition, a device may employ an AVD interval that causes both ventricles 106 and 108 to contract at a point time no later than that at which the right ventricle 106 would have intrinsically contracted. By capturing both ventricles 106 and 108, and causing them to contract substantially simultaneously, the waffling action of the septum 118 may be inhibited, thereby enhancing the overall contractility of the left ventricle. Such an AVD interval is a function of the propagation delays between the right atrium 102 and the right and left ventricles 106 and 108, or any signal or physiological event in predictable relation to such delays. In other words, $$AVD_{contractility} = f(RA-RV, RA-LV),$$

where $AVD_{contractility}$ represents an AVD interval maximizing left ventricular contractility for a given patient and lead configuration or pacing chamber, RA-RV represents a time interval during which an electrical impulse propagates between the right atrium and the right ventricle, and RA-LV represents a time interval during which an electrical impulse propagates between the right atrium and the left ventricle.

Figure 2:
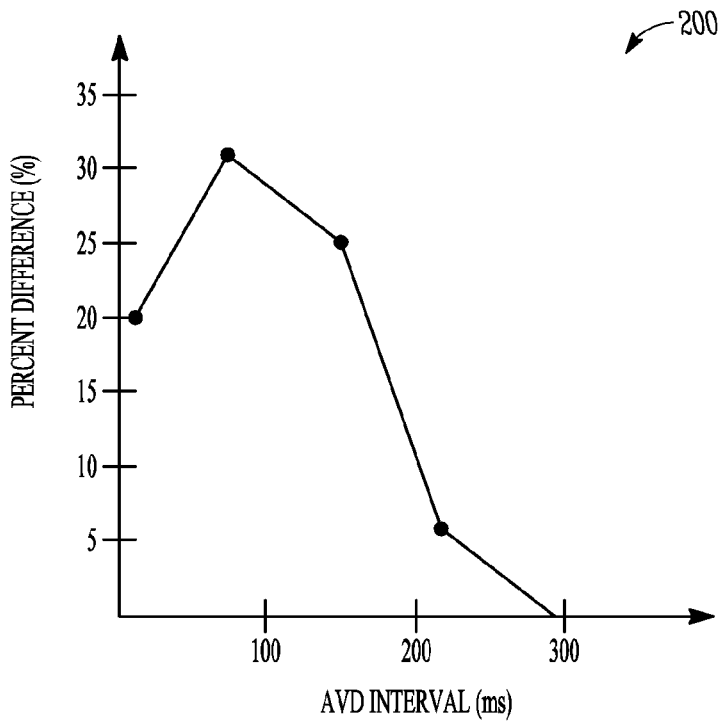
FIG. 2 depicts a chart relating changes in aortic pulse pressure to a range of AVD intervals.
Figure 3:
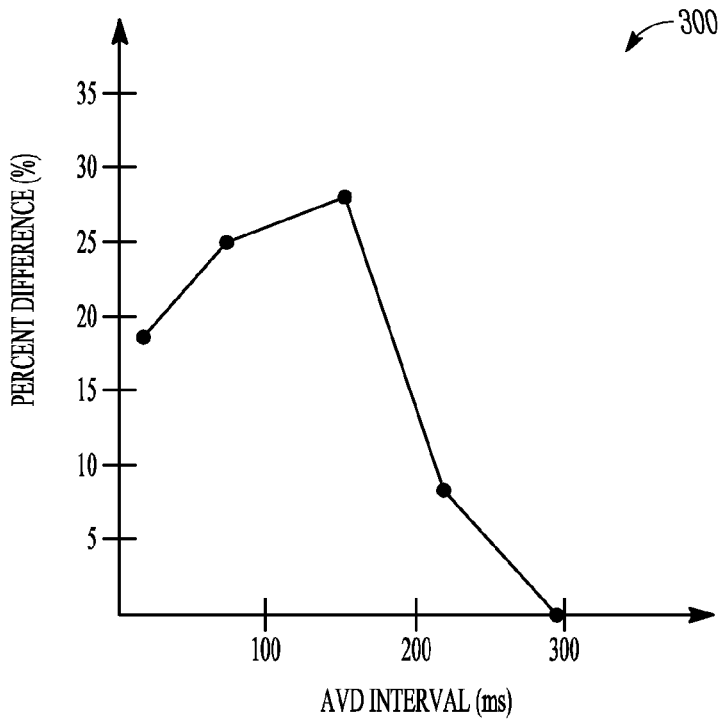
FIG. 3 depicts a chart relating changes in positive-going rates of change of left ventricular pressure over a range of AVD intervals.

The discussion (below) relating to FIGS. 2 and 3 presents data consistent with the notion that, for a given patient and pacing chamber, the AVD interval at which left ventricular contractility is maximized differs from that at which stroke volume is maximized.

Stroke volume is generally understood to correspond to aortic pulse pressure. Thus, for a given patient and pacing chamber, one may program a device to employ a range of AVD intervals and measure the resulting aortic pulse pressure. The AVD interval at which the maximum aortic pulse pressure is observed corresponds to the AVD interval at which the maximum stroke volume would be observed, if directly measured. In other words, aortic pulse pressure may be measured as a surrogate for stroke volume.

FIG. 2 depicts a chart 200 relating changes in aortic pulse pressure to a range of AVD intervals. The chart 200 is constructed from averaged data obtained over a populace of patients. Percent change in aortic pulse pressure is plotted along the y-axis. The AVD interval is plotted along the x-axis. As can be seen, the maximum positive change in aortic pulse pressure occurs at an AVD interval of about 80 milliseconds. Therefore, according to the chart 200 of FIG. 2, $AVD_{stroke\ volume}$=80 ms for the particular populace of patients and pacing chamber used in collecting the data presented therein.

Left ventricular contractility is generally understood to correspond to the positive-going change in left ventricular pressure per unit of time (denoted LV+dP/dt). Thus, for a given patient and pacing chamber, one may program a device to employ a range of AVD intervals, and may measure the resulting positive-going change in left ventricular pressure per unit of time. The AVD interval at which the maximum positive-going change in left ventricular pressure per unit of time is observed corresponds to the AVD interval at which the maximum left ventricular contractility would be observed, if directly measured. In other words, positive-going change in left ventricular pressure per unit of time may be measured as a surrogate for left ventricular contractility.

FIG. 3 depicts a chart 300 relating changes in positive-going rates of change of left ventricular pressure over a range of AVD intervals. Like the chart 200 of FIG. 2, the chart 300 of FIG. 3 is constructed from averaged data obtained from the same populace of patients used in collecting the data presented in FIG. 2. Percent change in the positive-going rate of change of left ventricular pressure is plotted along the y-axis. The AVD interval is plotted along the x-axis. As can be seen, the maximum change in the positive-going rate of change of left ventricular pressure occurs at an AVD interval of about 150 milliseconds. Therefore, according to the chart 300 of FIG. 3, $AVD_{contractility}$=150 ms for the particular populace of patients and pacing chamber used in collecting the data presented therein.

From FIGS. 2 and 3, it can be seen that $AVD_{stroke\ volume} \neq AVD_{contractility}$ for the particular populace of patients used to generate the data presented in those figures. Moreover, these figures suggest that the optimal AVD intervals for maximizing pulse pressure and LV+dP/dt may differ within an individual.

The implication of the data presented in FIGS. 2 and 3 is that a physician, when configuring a cardiac resynchronization therapeutic device for a patient, is faced with a choice: either configure the device to use an AVD interval intended to maximize stroke volume, or configure the device to use an AVD interval intended to maximize left ventricular contractility. Among other thins, the present inventors have recognized that one approach for resolving this dilemma is to present the physician with a range of intermediate AVD intervals between $AVD_{stroke\ volume}$ and $AVD_{contractility}$. Thus, for example, a physician may be presented with an option to select an AVD interval that is a weighted average of $AVD_{stroke\ volume}$ and $AVD_{contractility}$. This approach is discussed in further detail, below.

Using the raw data presented in FIG. 2, it has been determined that $AVD_{stroke\ volume}$ may be arrived at, for a given patient and lead configuration/pacing chamber, by the following formula:

$$AVD_{stroke\ volume} = K_1 * IAD + K_2,$$

where $K_1$ and $K_2$ are constants, and IAD represents the inter-atrial delay exhibited by a given patient's heart. Other formulas for $AVD_{stroke\ volume}$ are also suitable, such as those described in U.S. Pat. No. 6,144,880, which is incorporated by reference in its entirety, including such description.

The above-recited formula for $AVD_{stroke\ volume}$ is a function of inter-atrial delay. The inter-atrial delay exhibited by a heart may vary based upon whether the electrical impulse originated intrinsically (e.g., originated at the sinoatrial node), or originated from a pacing lead (i.e., the right atrium was paced). Thus, $AVD_{stroke\ volume}$ may be calculated separately for each source of origination—one such delay interval to follow an atrial sense and one delay interval to follow an atrial pace.

In one embodiment, the constants $K_1$ and $K_2$ in the above-recited formula are: $K_1$=1.22, and $K_2$=−133 milliseconds. Values for $K_1$ and $K_2$ are approximate and may vary. Further, these value may vary from patient to patient, and may vary with time. Still further, these values may vary with lead placement and/or pacing mode. Further yet, these values may vary as a function of conduction disorder type. All such variations are within the scope of the present invention.

The above-recited formula for $AVD_{stroke\ volume}$ requires measurement of the inter-atrial delay exhibited by a particular patient's heart. Many techniques to acquire the inter-atrial delay are known and are within the scope of the present invention. Some of the known techniques involve the use of equipment that is not normally present in the electrophysiology lab at the time of implantation of a pulse generator device. For the sake of convenience, it may be desirable to obtain the inter-atrial delay data using equipment that is normally present at the time of implantation. The following discussion presents schemes that permit the acquisition of the inter-atrial delay using equipment normally present at the time of implantation.

Ordinarily, one or more leads extend from a pulse generator into one or more of the various chambers of a patient's heart. Usually, the lead(s) gain entry into the heart by way of passing through the superior vena cava. For example, in the context of a pectoral implantation of a pulse generator device, a lead may be inserted into the subclavian vein and extended through that vein into the superior vena cava, whereupon the lead enters the right atrium of the heart. One or more electrodes on the lead used to pace and sense the right atrium are then implanted in the right atrium.

The lead used for pacing and sensing the right ventricle is advanced through the right atrium, and threaded through the tricuspid valve into the right ventricle. Again, one or more electrodes on the lead used to pace and sense the right ventricle are then implanted in therein.

To reach the left ventricle, a lead is advanced through the right atrium, and extended into the coronary sinus. Next, the left ventricular lead is threaded through the coronary sinus, and into the left ventricle. Then, one or more electrodes on the lead are implanted in the left ventricle.

While the left ventricular lead is advanced through the coronary sinus, an opportunity for sensing electrical activity in the left atrium emerges. Specifically, the left ventricular lead may be advanced to a position where the electrode(s) thereon are located at about the mid-coronary sinus. When the electrodes are located at about the mid-coronary sinus, they are physically located along a peripheral region of the left atrium, meaning that an electrical signal propagating through the left atrium may be detected. During implantation, the physician may halt the advancement of the left ventricular lead when the electrodes are at the aforementioned location. Then, the left ventricular lead may be used to detect electrical activity in the left atrium.

Figure 4:
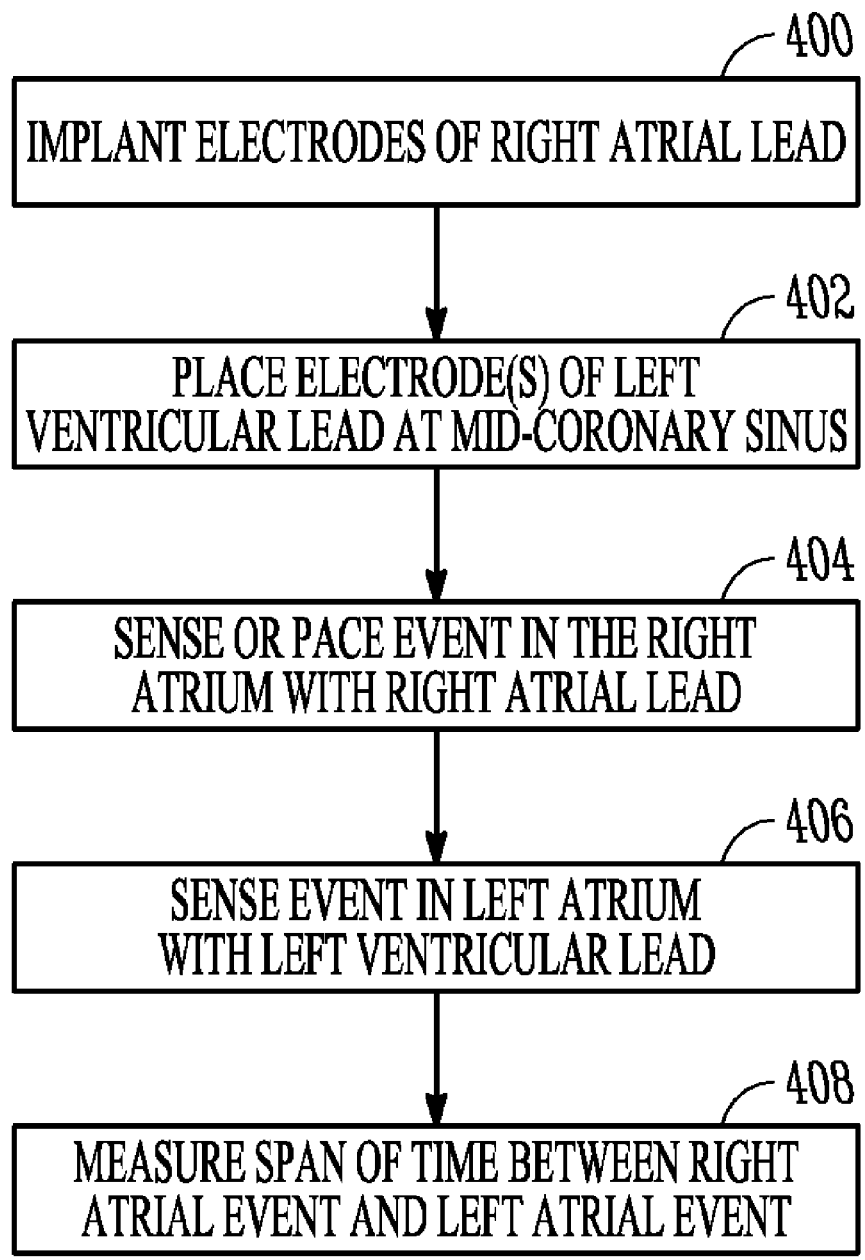
FIG. 4 depicts a scheme for determining inter-atrial delay, according to one embodiment of the present invention.

To obtain the inter-atrial delay, the physician may follow the procedure described by FIG. 4. As shown in FIG. 4, a lead is implanted in the right atrium in the standard manner (operation 400), and the left ventricular lead is placed at the mid-coronary sinus, as discussed above (operation 402). Thereafter, the right atrial lead may be used to pace or sense an event in the right atrium, as shown in operation 404. Then, the ensuing left atrial event is sensed using the left ventricular lead (operation 406). Finally, the span of time separating the paced or sensed event in operation 404 and the sensed event in operation 406 is measured, yielding an inter-atrial delay measurement at operation 408.

Because a patient's heart may exhibit different inter-atrial delays depending upon whether the right atrial event is paced or sensed, operations 404 through 408 may be performed once for a paced even and once for a sensed event. (Operations 404-408 may be performed a multiplicity of times for a paced event, and a multiplicity of times for a sensed event. The data resulting from operations 404-408 for each of the paced events may be averaged, to arrive at an average inter-atrial delay exhibited in the wake of a paced event. Similarly, the data resulting from operations 404-408 for each of the sensed events may be averaged, to arrive at an average inter-atrial delay exhibited in the wake of a sensed event.)

Figure 5:
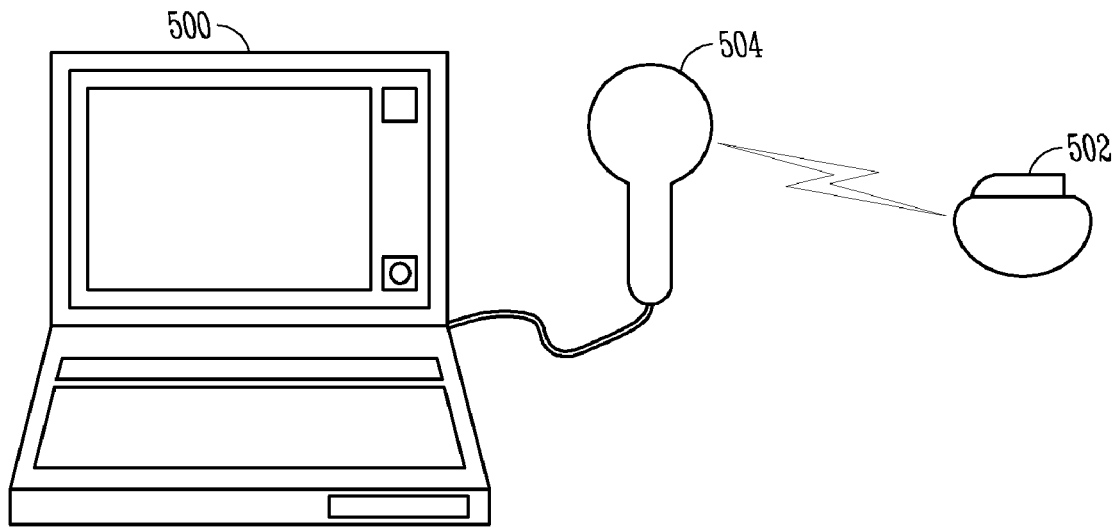
FIG. 5 depicts a programmer in communication with a pulse generator device.

During implantation of a pulse generator, operation 406 may be aided by a programmer unit. By way of background, during an implantation procedure, a physician may make use of a programmer unit 500, as depicted in FIG. 5. The programmer unit 500 may be a general-purpose computer, having a peripheral board (not depicted) that supports telemetry functionality. The programmer unit 500 communicates with a pulse generator device 502 by way of a telemetry wand 504 that is driven by the aforementioned peripheral board.

The programmer unit 500 may query the pulse generator 502 regarding its pacing parameters, for example. The programmer unit 500 may also command the pulse generator to perform certain actions, such as pace a particular chamber when a button is selected by the user of the programmer unit 500.

Figure 6:
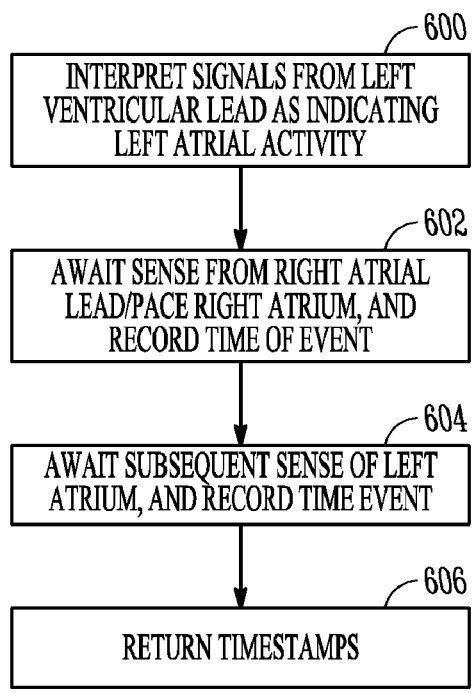
FIG. 6 depicts a mode of operation that may be invoked for measuring inter-atrial delay.

The programmer unit 500 may be programmed to provide an automatic scheme for measuring the inter-atrial delay. During implantation, the physician may invoke the automatic scheme, causing the programmer unit 500 to command the pulse generator device 502 to enter a mode of operation in which the acts depicted in FIG. 6 are executed. During the mode of operation, the pulse generator device 502 interprets the signals emanating from its left ventricular lead as indicating left atrial activity, as opposed to indicating left ventricular activity (operation 600). The pulse generator 502 may either await a sensed event from the right atrial lead, or may pace the right atrium (operation 602). The paced or sensed event in the right atrium is recorded and time-stamped by the pulse generator 502 (operation 602). Alternatively, the pulse generator device 502 may activate a timer upon occurrence of the paced or sensed event in the right atrium. Next, as shown in operation 604, the pulse generator device 502 awaits a sensed event in the left atrium (the event is detected via the left ventricular lead, as discussed previously). The sensed event in the left atrium is recorded and time-stamped by the pulse generator device 502 (operation 604). Alternatively, if the pulse generator device 502 had activated a timer during execution of operation 602, the timer may be halted during execution of operation 604. Finally, as shown in operation 606, the time-stamps recorded in operations 602 and 604 are returned to the pulse generator device 502. Alternatively, if a timer was activated/deactivated in lieu of recording and time-stamping the atrial events, the value of the timer may be returned to the programmer unit 500. Thus, in sum, the effect of operations 600-606 is to measure a span of time separating a paced or sensed event in the right atrium from the ensuing sensed event in the left atrium. In the wake of operation 606 having been performed, the pulse generator device 502 may return to interpreting signals emanating from the left ventricular lead as indicating left ventricular activity.

As an alternative, the programmer unit 500 may command the pulse generator unit 502 to stream real-time electrogram data or event markers to the programmer while the electrode(s) of the left ventricular lead are situated at about the mid-coronary sinus. Then, the programmer unit 500, instead of the pulse generator device 502, may execute operations 600-604. In other words, the programmer unit 500 may interpret the electrogram data or event markers in a manner such that signals emanating from the left ventricular lead are interpreted as indicating left atrial activity, instead left ventricular activity (operation 600). The programmer unit 500 awaits an indication in the electrogram data or event marker data of a sensed event in the right atrium, or commands a paced event therein (operation 602). Thereafter, the programmer unit 500 awaits an indication in the electrogram data or event marker data of a sensed left atrial event (operation 604). The programmer unit 500 finds the inter-atrial delay by measuring the time interval separating the events of operations 602 and 604, such as by starting/stopping a timer.

There exists yet another scheme by which a patient's inter-atrial delay may be determined. The scheme involves the use of a lead 700, depicted in schematic form in FIG. 7A. The lead 700 depicted in FIG. 7A includes a tip electrode 704 and a ring electrode 702. The tip electrode 704 and ring electrode 702 are separated by a distance $d_1$. The distance $d_1$ between the tip and ring electrodes 704 and 702 is of sufficient length that the ring electrode 702 may be situated at approximately the mid-coronary sinus, while the tip electrode 704 is placed within the left ventricle (e.g., left ventricular free wall or left ventricular anterior wall).

Figure 7A:
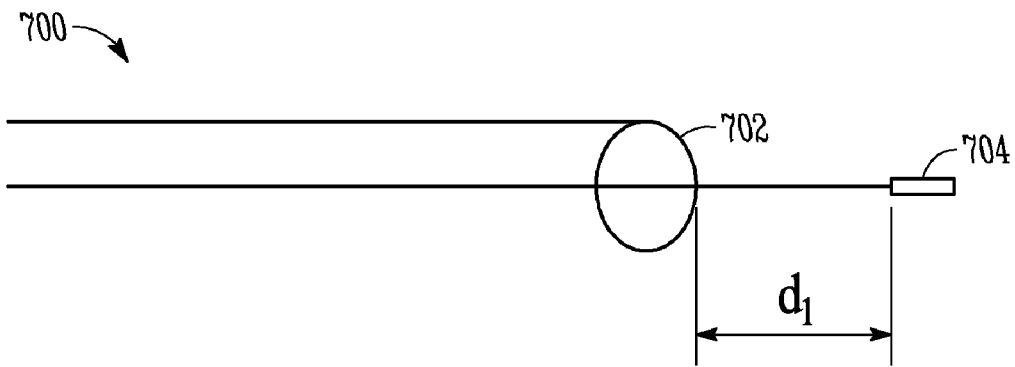
FIG. 7A depicts a lead for sensing the left atrium, according to one embodiment of the present invention.

During implantation, the lead 700 of FIG. 7A may be extended through the mid-coronary sinus to the left ventricle, as discussed above. The tip and ring electrodes 704 and 702 may be implanted in the left ventricle and mid-coronary sinus, respectively. During operation, each electrode 702 and 704 operates in a unipolar mode (i.e., sense and pace to the "can" electrode of the pulse generator device). Thus, given such an arrangement, the ring electrode 702 may be used to sense electrical activity in the left atrium. The ring electrode 702 senses such activity in a unipolar mode. Additionally, the tip electrode 704 may be used to sense and pace the left atrium. Again, the tip electrode 704 senses and paces in a unipolar mode.

Use of the lead 700 depicted in FIG. 7A permits the inter-atrial delay exhibited by a heart to be measured with each atrial event, if desired. With the occurrence of each such event, the pulse generator device 502 may measure the span of time between the sensed or paced event in the right atrium and the subsequent sensed event in the left atrium. Thus, a pulse generator device 502 using the lead 700 of FIG. 7A may recalculate $AVD_{stroke\ volume}$ with each paced or sensed event, or at designated intervals.

Figure 7B:
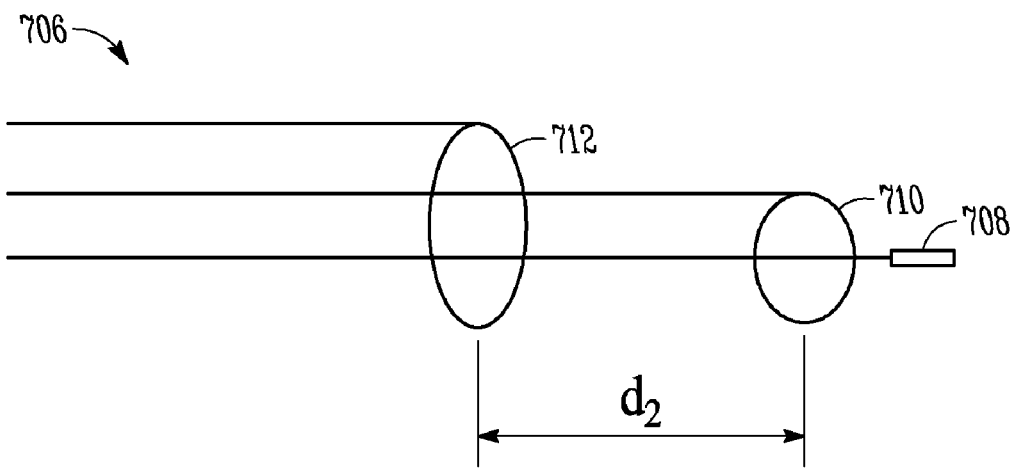
FIG. 7B depicts another lead for sensing the left atrium, according to one embodiment of the present invention.

As an alternative to the lead 700 of FIG. 7A, the lead 706 of FIG. 7B may be used. The lead 706 of FIG. 7B includes a tip electrode 708 and two ring electrodes 710 and 712. The tip electrode 708 and first ring electrode 710 are in proximity to one another, as are an ordinary tip/ring electrode pair. The tip 708 and ring 710 electrode pair may be used for pacing and sensing the left ventricle. Thus, pacing and sensing in the left ventricle may be performed in a bipolar mode (between tip and ring) or in a unipolar mode. As can be seen from FIG. 7B, the second ring electrode 712 is separated from the first ring electrode by a distance $d_2$. The distance $d_2$ between the first and second ring electrodes 710 and 712 is of sufficient length that the second ring electrode 712 may be situated at approximately the mid-coronary sinus, while the first ring electrode is placed within the left ventricle (e.g., left ventricular free wall or left ventricular anterior wall).

During implantation, the lead 706 of FIG. 7B may be extended through the mid-coronary sinus to the left ventricle, as discussed above. The tip 708 and ring 710 electrode pair may be implanted in the left ventricle, while the second ring electrode 712 may be implanted in the mid-coronary sinus. As mentioned above, during operation, the tip 708 and ring 710 electrode pair may operate in bipolar or unipolar mode. The second ring electrode 712 operates in a unipolar mode. Thus, given such an arrangement, the second ring electrode 712 may be used to sense electrical activity in the left atrium. The second ring electrode 712 senses such activity in a unipolar mode.

Use of the lead 706 depicted in FIG. 7B permits the inter-atrial delay exhibited by a heart to be measured with each atrial event, if desired. With the occurrence of each such event, the pulse generator device 502 may measure the span of time between the sensed or paced event in the right atrium and the subsequent sensed event in the left atrium. Thus, a pulse generator device 502 using the lead 706 of FIG. 7B may recalculate $AVD_{stroke\ volume}$ with each paced or sensed event, or at designated intervals.

Returning to the previous discussion of FIG. 3, based upon the raw data presented therein, it has been determined that $AVD_{contractility}$ may be arrived at, for a given patient and lead configuration by the following formula:

$$AVD_{contractility} = K_3 * QRS + K_4 * AVR + K_5,$$

where $K_3$, $K_4$, and $K_5$ are constants, QRS represents the width of the QRS complex, and AVR represents the span of time separating a paced or sensed right atrial event and a sensed right ventricular event.

The above-recited formula for $AVD_{contractility}$ is a function of the span of time separating a paced or sensed right atrial event and a sensed right ventricular event. It is also a function of the width of the QRS complex. As stated previously, for a given heart, these particular spans of time may vary based upon whether the electrical impulse originated intrinsically (e.g., originated at the sinoatrial node), or originated from a pacing lead (i.e., the right atrium was paced). Thus, $AVD_{contractility}$ may be calculated separately for each source of origination-one such delay interval to follow an atrial sense and one delay interval to follow an atrial pace.

The constants $K_3$, $K_4$ and $K_5$ in the above-recited formula may vary based upon lead placement. Thus, for example, when pacing only the left ventricle with a left ventricular anterior wall lead placement, $K_3=-1.325$, $K_4=0.918$, and $K_5=135.3$. When performing biventricular pacing with a left ventricular anterior wall lead placement, $K_3=-0.835$, $K_4=1.041$, and $K_5=49$. When pacing only the left ventricle with a left ventricular free wall lead placement, $K_3=-0.459$, $K_4=0.911$, and $K_5=-4.3$. Finally, when performing biventricular pacing with left ventricular free wall lead placement, $K_3=-0.728$, $K_4=0.757$, and $K_5=71.3$. Values for $K_3$, $K_4$ and $K_5$ are approximate and may vary. Further, these values may vary from patient to patient, and may vary with time. Still further, these values may vary with lead placement and/or pacing mode. Further yet, these values may vary as a function of conduction disorder type. All such variations are within the scope of the present invention.

When the span of time separating a paced or sensed right atrial event and a sensed left ventricular event (AVL) can be measured accurately, the following equation for $AVD_{contractility}$ may be used:

$$AVD_{contractility} = K_6 * AVL + K_7 * AVR + K_8,$$

where $K_6$, $K_7$, and $K_8$ are constants, AVR represents the span of time separating a paced or sensed right atrial event and a sensed right ventricular event, and AVL represents the span of time separating a paced or sensed right atrial event and a sensed left ventricular event. Other formulas for $AVD_{contractility}$ are also suitable, such as those described in U.S. Pat. No. 6,144,880, which is incorporated by reference herein in its entirety, including such description.

The above-recited formula for $AVD_{contractility}$ is a function of the span of time separating a paced or sensed right atrial event and a sensed right ventricular event. It is also a function of the span of time separating a paced or sensed right atrial event and a sensed left ventricular event. For a given heart, these particular spans of time may vary based upon whether the electrical impulse originated intrinsically (e.g., originated at the sinoatrial node), or originated from a pacing lead (i.e., the right atrium was paced). Thus, $AVD_{contractility}$ may be calculated separately for each source of origination—one such delay interval to follow an atrial sense and one delay interval to follow an atrial pace.

The constants $K_6$, $K_7$ and $K_8$ in the above-recited formula may vary based upon lead placement. Thus, for example, when pacing only the left ventricle with a left ventricular anterior wall lead placement, $K_6=0.163$, $K_7=0.769$, and $K_8=-59.6$. When performing biventricular pacing with a left ventricular anterior wall lead placement, $K_6=0.063$, $K_7=1.008$, and $K_8=-73$. When pacing only the left ventricle with a left ventricular free wall lead placement, $K_6=-0.099$, $K_7=0.988$, and $K_8=-64.3$. Finally, when performing biventricular pacing with a left ventricular free wall lead placement, $K_6=-0.126$, $K_7=0.857$, and $K_8=-27.5$. Values for $K_6$, $K_7$ and $K_8$ are approximate and may vary. Further, these value may vary from patient to patient, and may vary with time. Still further, these values may vary with lead placement and/or pacing mode. Further, these values may vary as a function of conduction disorder type. All such variations are within the scope of the present invention.

The preceding discussion has presented various schemes and formulas for arriving at $AVD_{contractility}$ and $AVD_{stroke\ volume}$. Other schemes may be employed for arriving at AVD intervals designed to optimize performance characteristics other than stroke volume and left ventricular contractility. What follows is a discussion of various methods for blending $AVD_{contractility}$ and $AVD_{stroke\ volume}$. By blending $AVD_{contractility}$ and $AVD_{stroke\ volume}$, it may be possible to arrive at an AVD interval that yields improved or optimal cardiac efficiency for left ventricular contractility and stroke volume, considered as a whole. The following blending schemes may be used to blend any set of calculated AVD intervals—not just $AVD_{contractility}$ and $AVD_{stroke\ volume}$.

One scheme for blending $AVD_{contractility}$ and $AVD_{stroke\ volume}$ is to find the arithmetic mean of the two figures:

$$AVD_{blended} = (AVD_{contractility} + AVD_{stroke\ volume})/2,$$

where $AVD_{blended}$ represents an AVD interval that is the result of blending $AVD_{contractility}$ and $AVD_{stroke\ volume}$. This calculation may be executed by the pulse generator device 502 or the programmer unit 500.

Another scheme for blending $AVD_{contractility}$ and $AVD_{stroke\ volume}$ is to find the geometric mean of the two figures:

$$AVD_{blended} = [(AVD_{contractility})(AVD_{stroke\ volume})]^{1/2}.$$

Again, this scheme may be performed by the pulse generator device 502 or the programmer unit 500.

Yet another scheme for blending $AVD_{contractility}$ and $AVD_{stroke\ volume}$ is to find a weighted average of the two figures:

$$AVD_{blended} = (K_5 * AVD_{contractility} + K_6 * AVD_{stroke\ volume})/(K_5 + K_6),$$

where $K_5$ and $K_6$ are coefficients that determine the relative weight with which each of $AVD_{contractility}$, $AVD_{stroke\ volume}$ are blended together.

A programmer unit 500 may be programmed to permit a physician to enter value for $K_5$ and $K_6$, so that the physician can determine the relative importance of each performance variable. For example, a physician may use the programmer unit 500 in the following manner. The programmer unit may present each of the proposed AVD interval values, i.e., $AVD_{contractility}$ and $AVD_{stroke\ volume}$. Upon inspect of the proposed AVD interval values, the physician may enter weight values to be applied to $AVD_{contractility}$ and $AVD_{stroke\ volume}$. For example, the physician may use the programmer unit 500 to select a weight of "8" for stroke volume, and a weight of "2" for contractility. Accordingly, the $AVD_{stroke\ volume}$ is given four times the weight given to $AVD_{contractility}$ in blending the two figures together. Again, the actual calculations may be performed by the pulse generator device 502 or the programmer unit 500.

What follows is an exemplary embodiment of a pulse generator device that may be used to employ any of the aforementioned schemes, and may be used with any of the aforementioned leads and lead configurations. Of course, other embodiments of pulse generator devices and are within the scope of the present invention, if employing any of the aforementioned schemes and lead configurations disclosed here.

Figure 8:
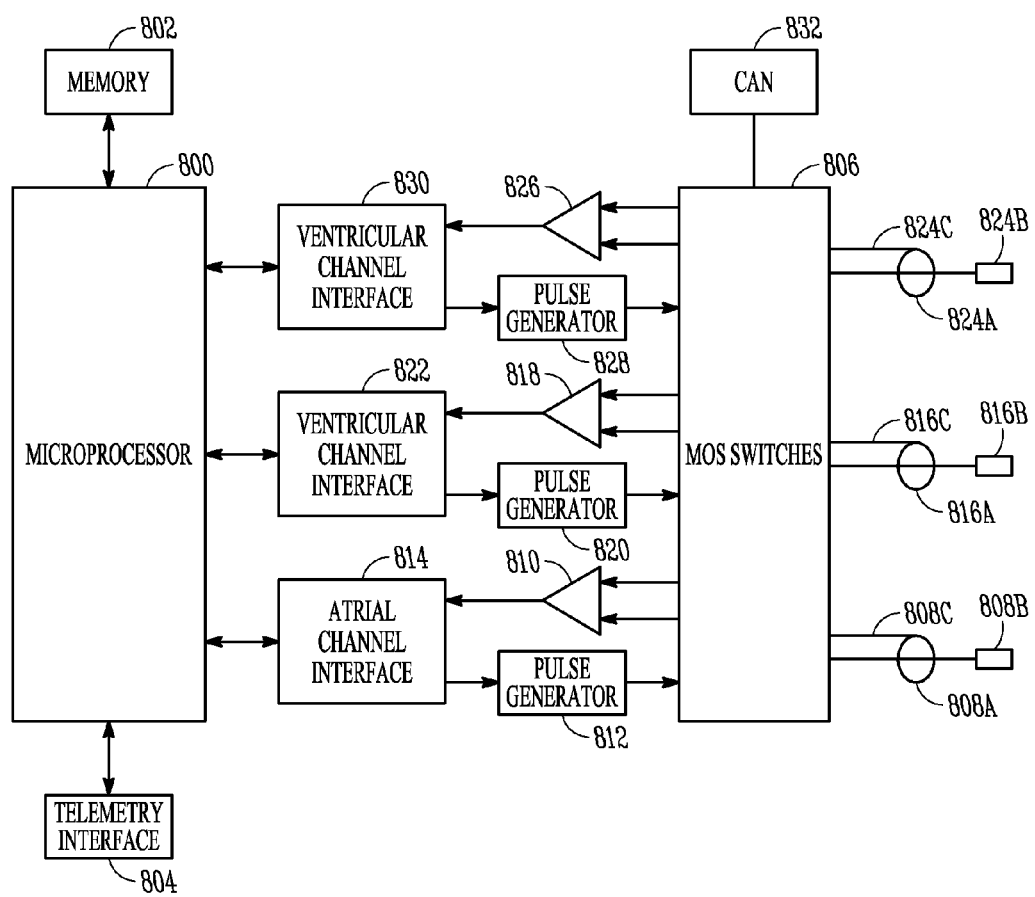
FIG. 8 depicts a pulse generator device that is an example of a suitable environment for incorporation of the methods, schemes, and leads disclosed herein.

A block diagram of a multi-site pacemaker having multiple sensing and pacing channels is shown in FIG. 8. (As the term is used herein, a "pacemaker" should be taken to mean any cardiac rhythm management device, such as an implantable cardioverter/defibrillator, with a pacing functionality.) The controller of the pacemaker is made up of a microprocessor 800 communicating with a memory 802 via a bidirectional data bus, where the memory 802 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 804 is also provided for communicating with an external programmer.

The embodiment shown in FIG. 8 has three sensing/pacing channels, where a pacing channel is made up of a pulse generator connected to an electrode while a sensing channel is made up of the sense amplifier connected to an electrode. A switching network 806 controlled by the microprocessor is used to switch the electrodes from the input of a sense amplifier to the output of a pulse generator. The switching network 806 also allows the sensing and pacing channels to be configured by the controller with different combinations of the available electrodes. The channels may be configured as either atrial or ventricular channels, allowing the device to deliver conventional ventricular single-site pacing with or without atrial tracking, biventricular pacing, or multi-site pacing of a single chamber. In an example configuration, a right atrial sensing/pacing channel includes ring electrode 808a and tip electrode 808b of bipolar lead 808c, sense amplifier 810, pulse generator 812, and a channel interface 814. A right ventricular sensing/pacing channel includes ring electrode 816a and tip electrode 816b of bipolar lead 816c, sense amplifier 818, pulse generator 820, and a channel interface 822, and a left ventricular sensing/pacing channel includes ring electrode 824a and tip electrode 824b of bipolar lead 824c, sense amplifier 826, pulse generator 828, and a channel interface 830. The channel interfaces communicate bi-directionally with a port of microprocessor 800 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 806 may configure a channel for unipolar sensing or pacing by referencing an electrode of a unipolar or bipolar lead with the device housing or can 832.

The controller 800 controls the overall operation of the device in accordance with programmed instructions stored in memory. The controller 800 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or ventricular sensing channel exceeds a specified threshold, the controller detects an atrial or ventricular sense, respectively, which pacing algorithms may employ to trigger or inhibit pacing. An electrogram is analogous to a surface ECG and indicates the time course and amplitude of cardiac depolarization that occurs during either an intrinsic or paced beat.

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

What is claimed is:

1. A system comprising:
a sensing circuit configured to: (1) detect at least one of a sensed or paced atrial event; and (2) detect a sensed ventricular event; and
a controller or programmer circuit, configured to be communicatively coupled to the sensing circuit, the controller or programmer circuit configured to: (1) determine a measured atrioventricular delay (AVD) concluded by the sensed ventricular event; (2) determine a measured interatrial delay (IAD) concluded by the sensed atrial event; (3) determine a first atrioventricular delay value, $AVD_1$, selected to approximately maximize contractility of a ventricle, using the measured AVD concluded by the sensed ventricular event; and (4) determine a second atrioventricular delay value, $AVD_2$, selected to approximately maximize stroke volume of the ventricle, using the measured IAD concluded by the sensed atrial event, wherein the controller or programmer circuit is configured to use a blended atrioventricular delay ($AVD_{blended}$) that is determined using a user-modifiable function of both $AVD_1$ and $AVD_2$, wherein the $AVD_{blended}$ is determined as an individually-scaled sum of $AVD_1$ and $AVD_2$.

2. The system of claim 1, wherein the controller or programmer circuit includes, or is configured to be communicatively coupled to, a user interface configured to receive user input and communicate output information to a user.

3. The system of claim 2, wherein the user interface is configured to receive user input including a first coefficient $K_5$ to be applied to $AVD_1$ and a second coefficient $K_6$ to be applied to $AVD_2$; and
wherein the controller or programmer circuit is configured to determine the blended atrioventricular delay according to $AVD_{blended} = (K_5 * AVD_1 + K_6 * AVD_2)/(K_5 + K_6)$.

4. The system of claim 2, wherein the user interface is configured to communicate an indication of at least one of $AVD_1$, or $AVD_2$, or $AVD_{blended}$ to a user.

5. The system of claim 1, comprising:
a first lead, configured to be communicatively coupled to the sensing circuit and the controller or programmer circuit, the first lead having an electrode configured to make electrical contact with a region in a right atrium of a heart; and
a second lead, configured to be communicatively coupled to the sensing circuit and the controller or programmer circuit, the second lead having an electrode configured to pass through and electrically contact a mid-coronary sinus of the heart before electrically contacting a left ventricle of the heart;
wherein the controller or programmer circuit is configured to perform a mode of operation, during which, a signal from the second lead is interpreted as indicating left atrial activity, and upon termination of the mode of operation, a signal from the second lead is interpreted as indicating left ventricular activity; and
wherein the controller or programmer circuit is configured to determine the IAD during the mode of operation using a time interval between a paced or sensed event in the right atrium, indicated by a signal from the first lead, and a sensed event in the left atrium, indicated by a signal from the second lead.

6. The system of claim 5, comprising a third lead, configured to be communicatively coupled to the sensing circuit and the controller or programmer circuit, the third lead having an electrode configured to make electrical contact with a region within a right ventricle of the heart;
wherein the controller or programmer circuit is configured to determine the AVD upon termination of the mode of operation using, at least in part, a time interval between a paced or sensed event in the right atrium, indicated by a signal from the first lead, and a sensed event in the left ventricle, indicated by a signal from the second lead; and
wherein the controller or programmer circuit is also configured to determine the AVD using, at least in part, a time interval between a paced or sensed event in the right atrium, indicated by a signal from the first lead, and a sensed event in the right ventricle, indicated by a signal from the third lead.

7. The system of claim 5, wherein the controller or programmer circuit includes, or is configured to be communicatively coupled to, a user interface configured to permit a user of the controller or programmer circuit to initiate the mode of operation.

8. The system of claim 1, wherein the ventricle is the left ventricle, and wherein peak positive left ventricular pressure change is used as a measurable indicator of contractility of the left ventricle.

9. The system of claim 1, wherein aortic pulse pressure is used as a measurable indicator of stroke volume.

10. The system of claim 1, wherein the controller or programmer circuit is configured to determine $AVD_1$ using, at least in part, a time interval between a paced or sensed event in the right atrium and a sensed event in a right ventricle; and wherein the controller or programmer circuit is also configured to determine $AVD_1$ using, at least in part, a time interval between a paced or sensed event in the right atrium and a sensed event in the left ventricle.

11. The system of claim 10, wherein the controller or programmer circuit is configured to determine $AVD_1$ using the formula $AVD_1 = K_1 * AVR + K_2 * AVL$,
wherein $K_1$ is a constant, AVR represents the time interval between a paced or sensed event in the right atrium and a sensed event in the right ventricle, $K_2$ is a constant, and AVL represents the time interval between a paced or sensed event in the right atrium and a sensed event in the left ventricle.

12. The system of claim 1, wherein the controller or programmer circuit is configured to determine $AVD_2$ using, at least in part, a time interval between a paced or sensed event in the right atrium and a sensed event in the left atrium.

13. The system of claim 12, wherein the controller or programmer circuit is configured to determine $AVD_2$ using the formula $AVD_2 = K_3 * IAD + K_4$,
wherein $K_3$ is a constant, IAD represents the time interval between the paced or sensed event in the right atrium and the sensed event in the left atrium, and $K_4$ is a constant.

14. The system of claim 1, comprising a pacing circuit configured to be programmed by the controller or programmer circuit to provide cardiac electrostimulation pulses according to $AVD_{blended}$.

15. The system of claim 1, wherein the controller or programmer circuit is configured to determine $AVD_1$ using a detected right atrial pace or sensed depolarization and a detected mid-coronary sinus left ventricular pace or sensed depolarization.

16. The system of claim 1, wherein the controller or programmer circuit is configured to determine the IAD by measuring a time interval between a paced or sensed event in the right atrium and a signal indicating left atrial activity; and wherein the controller or programmer is configured to use the IAD to determine $AVD_{blended}$.

17. The system of claim 1, wherein the controller or programmer circuit is configured to determine $AVD_1$ using at least one of: (1) a function of a time interval, AVR, between a paced or sensed event in the right atrium and a sensed event in the right ventricle; or (2) a function of a time interval, AVL, between a paced or sensed event in the right atrium and a sensed event in the left ventricle.

18. The system of claim 1, wherein the controller or programmer circuit is configured to determine $AVD_1$ using a function of a QRS width.

19. The system of claim 18, wherein the controller or programmer circuit is configured to determine $AVD_1$ using the equation $AVD_1 = K_3*QRS + K_4*AVR + K_5$, wherein $K_3$, $K_4$, and $K_5$ are constants, QRS represents the width of the QRS complex, and AVR represents a time interval between a paced or sensed right atrial event and a sensed right ventricular event.

20. A system comprising:
a sensing circuit configured to: (1) detect at least one of a sensed or paced atrial event; and (2) detect a sensed ventricular event; and
a controller or programmer circuit, configured to be communicatively coupled to the sensing circuit, the controller or programmer circuit configured to: (1) determine a measured atrioventricular delay (AVD) concluded by the sensed ventricular event; (2) determine a measured interatrial delay (IAD) concluded by the sensed atrial event; (3) determine a first atrioventricular delay value, $AVD_1$, selected to approximately maximize contractility of a ventricle, using the measured AVD concluded by the sensed ventricular event; and (4) determine a second atrioventricular delay value, $AVD_2$, selected to approximately maximize stroke volume of the ventricle, using the measured IAD concluded by the sensed atrial event, wherein the controller or programmer circuit is configured to use a blended atrioventricular delay ($AVD_{blended}$) that is determined using a user-weightable function of both $AVD_1$ and $AVD_2$;
a pacing circuit configured to be programmed by the controller or programmer circuit to provide cardiac electrostimulation pulses according to $AVD_{blended}$; and
wherein the $AVD_{blended}$ is determined according to $AVD_{blended} = (K_5*AVD_1 + K_6*AVD_2)/(K_5+K_6)$.

* * * * *